(12) United States Patent
Yano et al.

(10) Patent No.: US 9,766,190 B2
(45) Date of Patent: Sep. 19, 2017

(54) METHOD, SYSTEM AND APPARATUS FOR MEASURING COMPARATIVELY THICK MATERIALS

(71) Applicants: TOYOTA JIDOSHA KABUSHIKI KAISHA, Toyota-shi, Aichi-ken (JP); INTER-UNIVERSITY RESEARCH INSTITUTE CORPORATION HIGH ENERGY ACCELERATOR RESEARCH ORGANIZATION, Tsukuba-shi, Ibaraki (JP)

(72) Inventors: Masao Yano, Sunto-gun (JP); Kanta Ono, Tsukuba (JP)

(73) Assignees: TOYOTA JIDOSHA KABUSHIKI KAISHA, Toyota (JP); INTER-UNIVERSITY RESEARCH INSTITUTE CORPORATION HIGH ENERGY ACCELERATOR RESEARCH ORGANIZATION, Ibaraki (JP)

( * ) Notice: Subject to any disclaimer, the term of this patent is extended or adjusted under 35 U.S.C. 154(b) by 173 days.

(21) Appl. No.: 14/496,966

(22) Filed: Sep. 25, 2014

(65) Prior Publication Data
US 2015/0084622 A1    Mar. 26, 2015

(30) Foreign Application Priority Data

Sep. 25, 2013    (JP) .................................. 2013-198163

(51) Int. Cl.
*G01N 27/72* (2006.01)
*G01N 23/06* (2006.01)
*G01N 23/04* (2006.01)

(52) U.S. Cl.
CPC ........... *G01N 23/063* (2013.01); *G01N 23/04* (2013.01); *G01N 27/72* (2013.01); *G01N 2223/405* (2013.01)

(58) Field of Classification Search
CPC ................. G01N 23/063; G01N 27/72; G01N 2223/405; G01N 23/04
(Continued)

(56) References Cited

U.S. PATENT DOCUMENTS 3,967,902 A * 7/1976 Steinberg ........... G01N 21/6445
                                                      250/225
4,003,663 A * 1/1977 Steinberg ............... G01N 21/21
                                                      356/243.1
(Continued)

FOREIGN PATENT DOCUMENTS

JP    A-5-45304         2/1993
JP    H05-045304 A      2/1993
(Continued)

OTHER PUBLICATIONS

Ono et al., "Element-Specific Magnetic Domain Imaging of (Nd, Dy)—Fe—B Sintered Magnets Using Scanning Transmission X-Ray Microscopy," IEEE Transactions on Magnetics, Oct. 2011, vol. 47, No. 10, pp. 2672-2675.
(Continued)

*Primary Examiner* — Jay Patidar
(74) *Attorney, Agent, or Firm* — Oliff PLC (57) ABSTRACT

A method, system and apparatus are provided to measure magnetic characteristics of a comparatively thick magnetic sample in a magnetic field or nonmagnetic field by X-ray magnetic circular dichroism (XMCD). In particular, the method, system and apparatus measure the magnetic char-
(Continued)

acteristics of the thick magnetic sample by irradiating the sample with X-ray, and detecting transmissive X-ray passing through the sample.

20 Claims, 9 Drawing Sheets

(58) Field of Classification Search
USPC .............................................. 324/228, 224.1
See application file for complete search history.

(56) References Cited

U.S. PATENT DOCUMENTS

| | | | | |
|---|---|---|---|---|
| 6,389,101 | B1* | 5/2002 | Levine | G01N 23/046 378/145 |
| 6,917,472 | B1* | 7/2005 | Yun | G02B 3/08 359/355 |
| 2004/0246479 | A1* | 12/2004 | Cartlidge | G01N 21/6458 356/335 |
| 2009/0135486 | A1* | 5/2009 | McNulty | G02B 21/14 359/565 |
| 2015/0174272 | A1* | 6/2015 | Velez Tirado | A61K 49/1863 424/9.3 |

FOREIGN PATENT DOCUMENTS

| | | |
|---|---|---|
| JP | 2004-37204 A | 2/2004 |
| JP | A-2010-151455 | 7/2010 |
| JP | 2010-278682 A | 12/2010 |
| JP | A-2011-66005 | 3/2011 |
| JP | 2011-257318 A | 12/2011 |
| JP | A-2012-145533 | 8/2012 |

OTHER PUBLICATIONS

Alvarenga et al., "X-ray Magnetic Circular Dichroism in Fe/NiO Thin Films," Journal of Magnetism and Magnetic Materials, 2001, vol. 233, pp. 74-77.

Schütz et al., "Absorption of Circularly Polarized X Rays in Iron," *Physical Review Letters*, 1987, vol. 58 No. 7, Feb. 16, 1987, pp. 737-740.

"3D Nano-ESCA Station," *University of Tokyo*.

"Transmission Electron Microscope of Surface of Roll Fabricated by Focused Ion Beam," *JFE Techno-Research Corporation*.

Yoshio Suzuki, "Hard X-ray Microbeam with Sputtered-sliced Fresnel Zone Plate", The Japanese Society for Synchrotron Radiation Research; 1997.

* cited by examiner

METHOD, SYSTEM AND APPARATUS FOR MEASURING COMPARATIVELY THICK MATERIALS

CROSS-REFERENCE TO RELATED APPLICATIONS

This application is based on and claims the benefit of priority Japanese Patent Application No. JP2013-198163, filed on Sep. 25, 2013, the entire contents of which are incorporated herein by reference.

TECHNICAL FIELD

The present invention relates to the magnetic measurement method and its system and apparatus.

BACKGROUND

The Paper 1 has reported the original X-ray magnetic circular dichroism as follows: a magnetic sample is placed in the external strong magnetic field, an internal magnetization direction of the magnetic sample is aligned with one direction, then the sample is irradiated with circular polarization X-ray while the external magnetic field direction is alternately inverted, resultantly, intensity of transmission X-ray passing the sample is changed in accordance with whether the external magnetic field direction is parallel or anti-parallel to the polarization light direction, the intensity change appears remarkably at a neighborhood of X-ray absorption edge for the constituent element of the magnetic sample. Applying the above X-ray magnetic circular dichroism, very old method such as the patent literature 1 has been presented to observe magnetic samples. The patent literature 1 presented the method and apparatus to observe magnetic domain by X-ray magnetic circular dichroism (XMCD) as follows: the intensity ($I_0$) of incident X-ray and intensity ($I_t$) of transmission X-ray passing the sample are measured, $\mu_R \times t = \ln(I_0/I_t)$ and $\mu_L \times t = \ln(I_0/I_t)$ are calculated using the observed intensity ($I_0$) and observed intensity ($I_t$), $M = (\mu_R \times t - \mu_L \times t)/(\mu_R \times t + \mu_L \times t) = (\mu_R - \mu_L)/(\mu_R + \mu_L)$ is calculated using [$\mu_R \times t$] and [$\mu_L \times t$], and M is transformed into electronic signal for imaging, here, $\mu_R$ and $\mu_L$ are X-ray absorption coefficient for right-circular polarization X-ray and left-circular polarization X-ray, respectively, and t is thickness of the sample. However the method was impracticable because focusing of X-ray is no good, sensitivity of X-ray detection is very low, and X-ray transmittance for right-circular polarization X-ray and left-circular polarization X-ray are calculated from observed X-ray intensity $\ln(I_0/I_t)$ but indirectly observed.

Observation, structural analysis and elemental analysis of the structures and chemical and physical states of magnetic sample surfaces or their neighborhood have been studied using the secondary electrons which are emitted from the sample surfaces by irradiating the observed areas of the sample with electron beams or exciting light. For example, the patent literature 2 presented the method to form observation images of microscopic structures of the sample. However, the above conventional method has included several difficult problems: (1) the conventional method is merely able to observe magnetic characteristics in the region from uppermost surfaces of the sample to several nanometers in depth but unable to observe them over several nanometers in depth because any electrons to generate from places deeper than several nanometers cannot get out of the sample surfaces. Because, the method is the one to detect the secondary electrons that are emitted from the magnetic sample on absorption of synchrotron radiation light, (2) the conventional method has essentially undesirable problem that the observed analytical result does not always show true magnetic properties of the bulk due to interruption effect of oxidized layers in the uppermost surfaces, (3) the conventional method is undesirable to observe the magnetic sample within magnetic field because of an applied magnetic field to exert influence on the detection of the secondary electrons. From these reasons, it has been very difficult to measure in precise the magnetized structure in the inside of microparticles.

CONVENTIONAL ART

[Paper 1] Physical Review Letters, vol. 58, pp. 737-740 (1987)
[Patent Literature 1] JP-A-1993-045304
[Patent Literature 2] JP-A-2010-151455

DISCLOSURE OF THE INVENTION

Problems to be Solved by the Invention

The magnetic characteristic of magnetic body is almost determined by the magnetic properties in the micro-region. Therefore, it is necessary for the development of new magnetic materials to assign magnetic properties of the micro-particles. The conventional methods such as the above patent literature 1, Kerr effect microscope, magnetic force microscope, photo-electron microscope and the like, which have been known to obtain the magnetic information such as magnetic domain and magnetic moment, make it possible to observe the magnetic properties in the uppermost sample surfaces or averaged magnetic properties of polycrystalline materials. However, the conventional methods have been unable to observe even the magnetic properties of a single micro-particle as explained above.

The object of the present invention is, in view of the above described circumstances, to provide the method, system and apparatus that are capable of measuring true magnetic characteristic of crystal grains composing magnetic polycrystalline materials.

Measure for Solving the Problem

To achieve the above object, the present invention provides the method, system and apparatus that are capable of measuring the magnetic characteristic of sample within external magnetic field by X-ray magnetic circular dichroism. In particular, the present invention provides the method, system and apparatus to measure accurately and directly magnetic characteristic of very thick samples of 1 μm.

Advantages of the Invention

The present invention is able to directly measure transmittance of transmission X-ray passing the sample placed within external magnetic field, using the Avalanche photodiode to measure photo-count of X-ray magnetic circular dichroism. Therefore, the present invention makes it possible to carry out high sensitive and high precise measurement of magnetic sensitivity, magnetic state and magnetic structure of the bulk sample. Accordingly, the present invention makes it possible to measure the magnetic characteristic of single crystal grains in the sample of 50 nm~1000 nm in thickness.

EMBODIMENTS FOR CARRYING OUT THE INVENTION

First, the sample to be measured is cut into a microtome section of 50 nm~1000 nm in thickness. Preferable thickness of microtome section can be determined mainly by sample material, kinetic energy of used X-ray and transmittance of X-ray. For the present invention, a use of X-ray transmittance of 1% or more is sufficient for the measurement of micro-crystal grains. The thickness of microtome section is preferably 1000 nm or less, more preferably 50 nm~100 nm. The preparation of the microtome section of 50 nm~100 nm in thickness makes it possible to measure magnetic characteristic of micro-crystal grains and imaging with resolution of 100 nm or less, accordingly makes it possible to study local magnetic sensitivity induced by an applied magnetic field.

Figure 1:
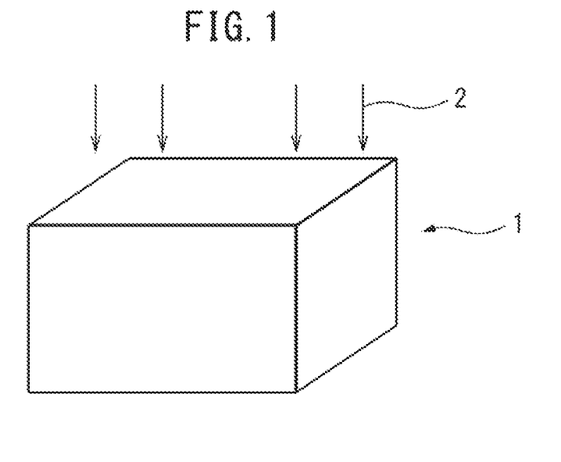
FIG. 1 is a cross-eye view showing the sample before etching.
Figure 2:
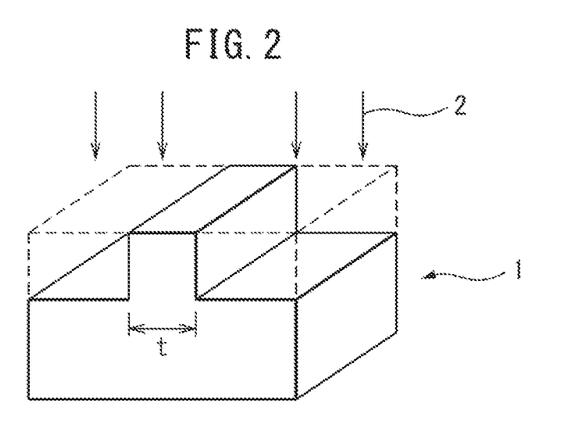
FIG. 2 is a cross-eye view showing the sample after etching.

For the preparation of microtome section, various methods can be used. For the preparation of microtome section of 1000 nm or less, the etching using focused ion beams is preferable. For example, the sample 1 as shown in FIG. 1 is etched using the focused ion beam 2, followed by obtaining a microtome section 1000 nm or less thick as shown in FIG. 2.

As the sample, various materials, for example, soft magnetic materials, hard magnetic materials, magnetic materials with plural magnetic phases, can be applied. As an apparatus to generate the focused ion beam 2, a usual focused ion beam machine comprising an ion beam gun and optic system to generate Ga-ion beams and scanning system to scan ion beams on the sample surfaces can be utilized.

Figure 3:
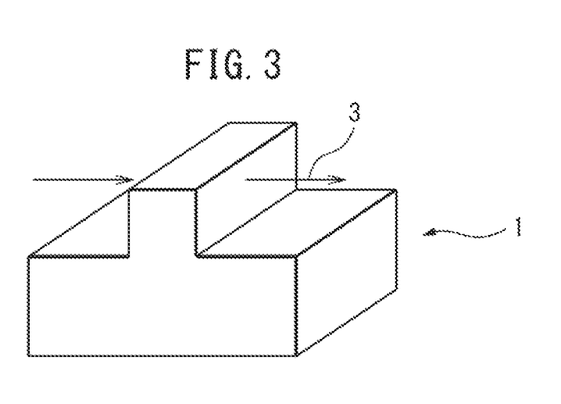
FIG. 3 is a cross-eye view showing the observation process.

After etching the sample using the focused ion beam 2, an observation place is irradiated with the X-ray 3, followed by detection the transmission X-ray to measure magnetic characteristic of the sample.

X-ray to be applied the sample is preferably circular polarization X-ray focused into 10 nm in beam size. In practice, the X-ray 3 generated by an X-ray generator which is capable of generating right-circular polarization X-ray and left-circular polarization X-ray enters a measurement place of the sample 1, successively the transmission X-ray is detected by a detector. The intensity IR of the transmission X-ray corresponding to right-circular polarization X-ray and the intensity IL of the transmission X-ray corresponding to left-circular polarization X-ray are alternately measured, successively the difference between them, that is, XMCD, can be detected. This measurement is corresponding to the magnetization in the inside of the X-ray incident position. Successively, the same measurement is carried out while two-dimensional (2-D)-scanning the sample, thus a 2-D-data is obtained. As another method, the X-ray absorption parallel to the magnetic field direction of the sample and that in the anti-parallel direction are measured using either right-circular polarization X-ray or left-circular polarization X-ray, the difference between them, that is, XMCD, can be also measured.

Figure 4:
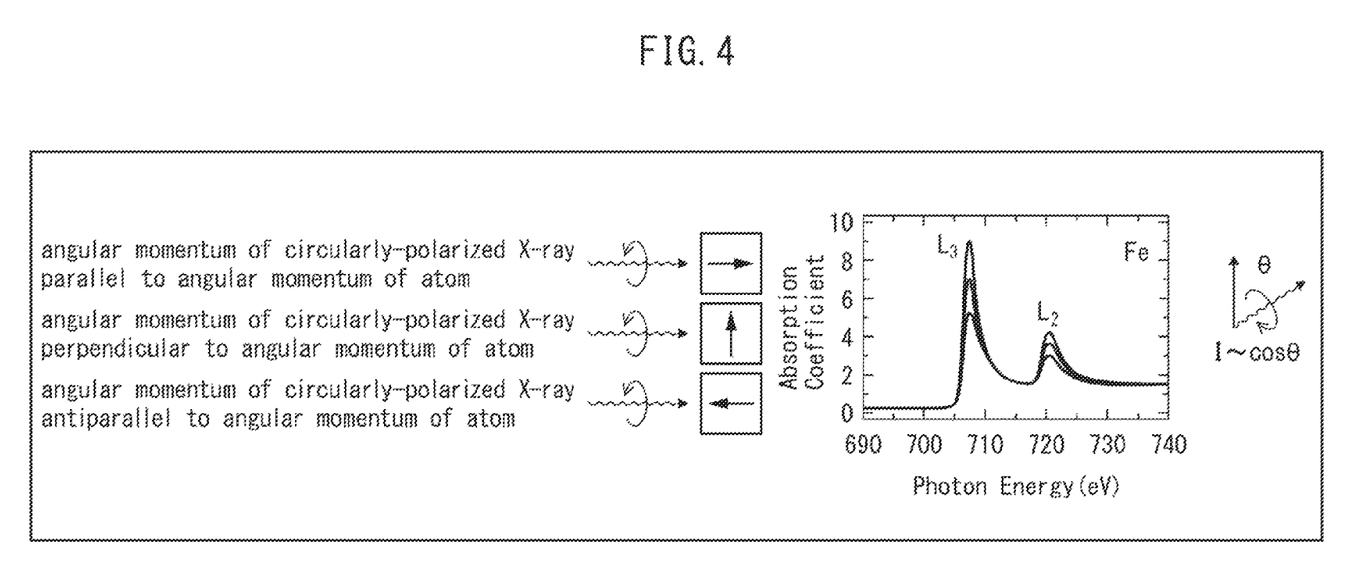
FIG. 4 is a schematic view illustrating the principle of X-ray magnetic circular dichroism (XMCD).

Further explaining in detail, magnetic information can be obtained using the principle of XMCD as shown in FIG. 4. The method has the element-selectivity, that is, the method is capable of measuring the direction of magnetic moment for a specific element by adjusting X-ray energy with an excitation energy gap between specific electron orbital.

As shown in FIG. 4, an absorption spectrum changes in accordance with the direction of angular momentum of circular polarization light and the direction of angular momentum of atom. The basic magnetic properties such as orbital angular momentum, spin angular momentum and magnetic momentum can be measured from (1) the measurement of angular momentum of circular polarization X-ray and that of atom in the case both momentums are parallel; (2) the measurement of angular momentum of circular polarization X-ray and that of atom in the case both momentums are anti-paralle; (3) the difference between them, that is, XMCD.

Figure 5:
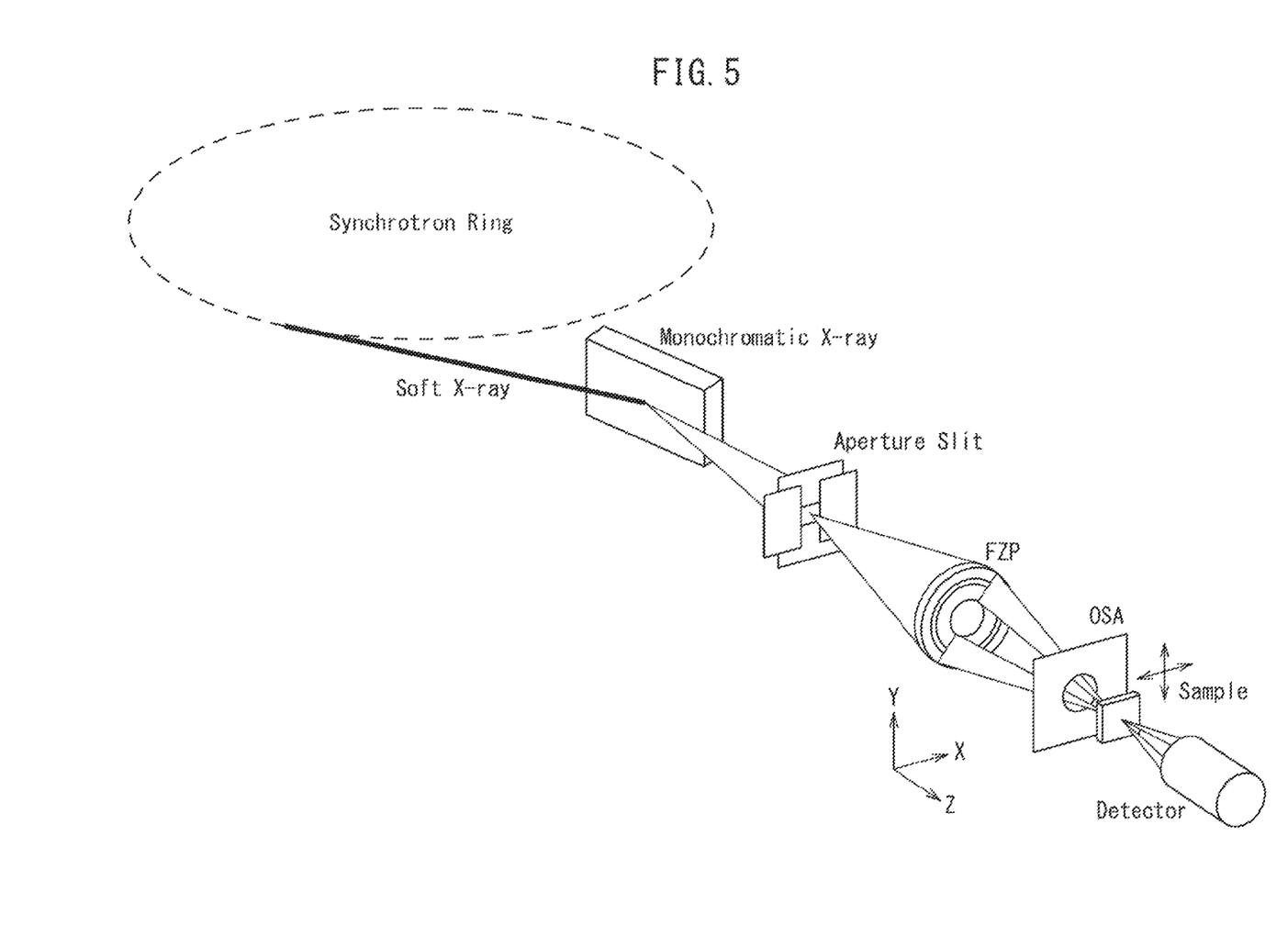
FIG. 5 is a configuration of the present apparatus equipping a scanning transmission electron microscope to carry out the present method.

As shown in FIG. 5, the present measurement system comprises a radiation source, a monochromator to disperse white radiation into monochromatic X-ray, an aperture slit to enter X-ray of the radiation source into an analytical section, the analytical section equipping a combination of Fresnel zone plate and order-sorting aperture to focus X-ray flux passing the aperture slit, a sample-stage to set a sample to be irradiated with X-ray and an X-ray-detector to detect transmission X-ray passing the sample; which is characterized by the measurement of X-ray magnetic circular dichroism of X-ray passing the sample within magnet field or nonmagnetic field. The XMCD at each sample place can be measured through precisely scanning the sample stage and using focused radiation light.

Figure 6:
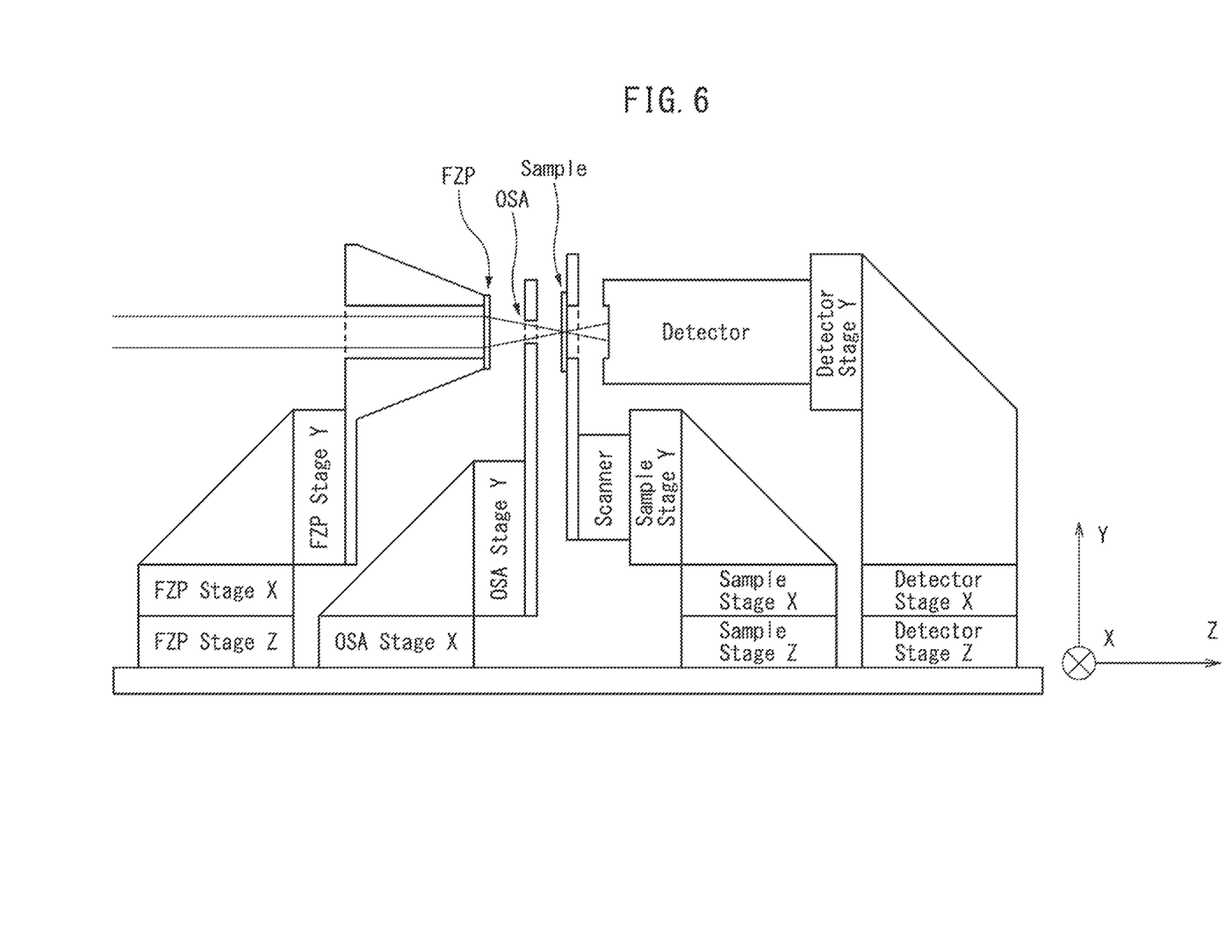
FIG. 6 is a configuration of the present apparatus to carry out the present method.

As shown in FIG. 6, the present measurement apparatus comprises the aperture slit, the analytical section equipping a combination of Fresnel zone plate (FZP) and order-sorting aperture (OSA) to focus X-ray flux passing the aperture slit, the sample-stage to set a sample to be irradiated with X-ray and the X-ray-detector equipping the Avalanche photodiode to detect transmittance of transmission X-ray passing the sample. The FZP, OSA, sample-stage and X-ray-detector are equipping piezoelectric devices, therefore their X-, Y- and Z-stages can be controlled to an accuracy of nanometers. For the efficient X-ray detection under a vacuum and magnetic field, the Avalanche photodiode (APD) having dynamic ranges and optical fibers which is used within external magnetic field is preferable. Also, the exclusion of heat-generating parts such as mortars and laser prevents the resolution of APD from thermal drift. Therefore, such exclusion is necessary to measure XMCD of a single particle in the nano-crystalline magnet. In addition, for the measurement in the magnetic field, a combination system of superconductive magnet and use of non-magnetic parts and devices is preferable.

A bulk sample of $Nd_2Fe_{14}B$ or $Sm_2Fe_{17}N_3$ is used as the sample. The sample is fabricated using focused ion beams, followed by measuring X-ray transmittance at each sample position. The measurement of X-ray transmittance for the $Nd_2Fe_{14}B$ sample or $Sm_2Fe_{17}N_3$ sample is based on the Nd-absorption-edge X-ray energy (980.4 eV) or Sm-absorption-edge X-ray energy (1083.3 eV), respectively. The result is shown in FIG. 7.

Figure 7:
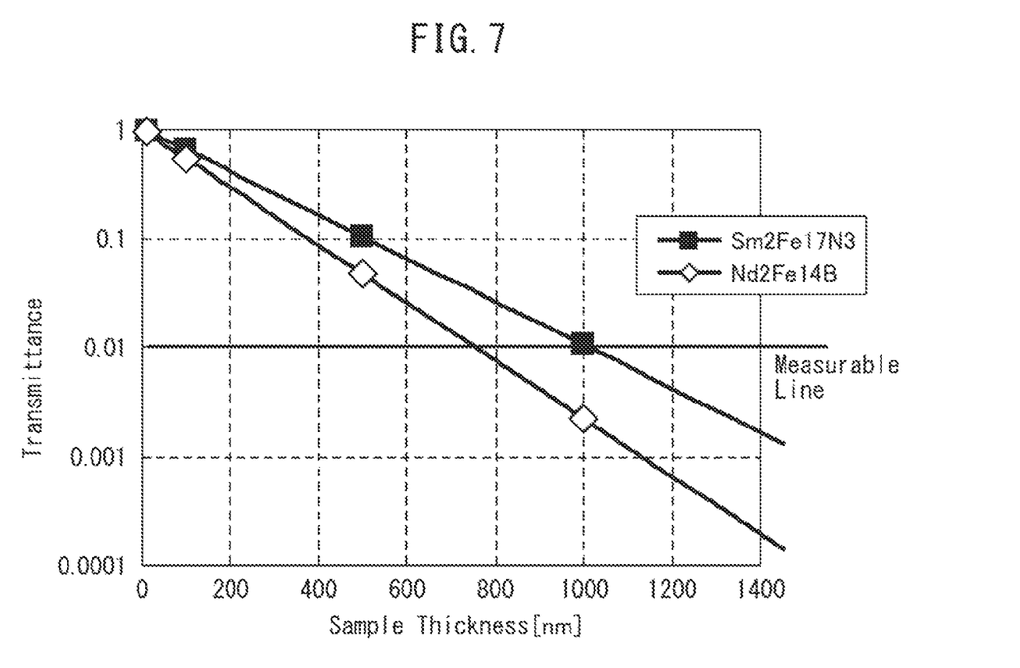
FIG. 7 shows a relationship between X-ray transmittance and thickness of the sample.

From the result of FIG. 7, it is found that the $Nd_2Fe_{14}B$ sample is measurable in the range 750 nm or less, 500 nm or less, 100 nm or less in thickness and that the $Sm_2Fe_{17}N_3$ sample is measurable in the range 1000 nm or less, 500 nm or less, 100 nm or less in thickness.

Figure 8:
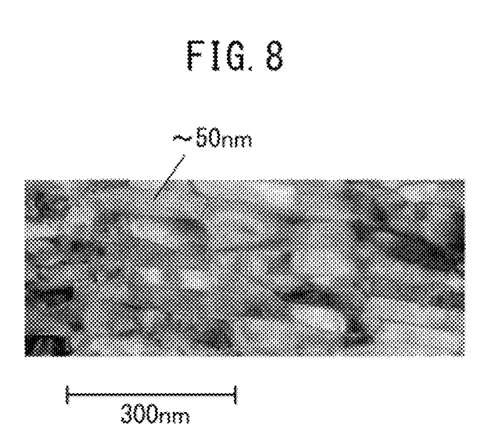
FIG. 8 is a transmission electron microscope (TEM) image of the sample plane.

A bulk sample of Nd—Fe—B magnet is used for the sample. A TEM image (FIG. 8) of lateral face of the sample is observed. From FIG. 8, the observed crystalline particle is estimated to be about 50 nm~100 nm in size.

Figure 9:
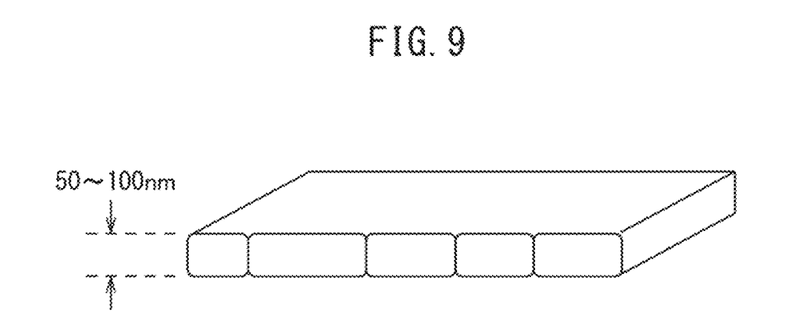
FIG. 9 is a cross-eye view showing a sample geometry after processing.
Figure 10:
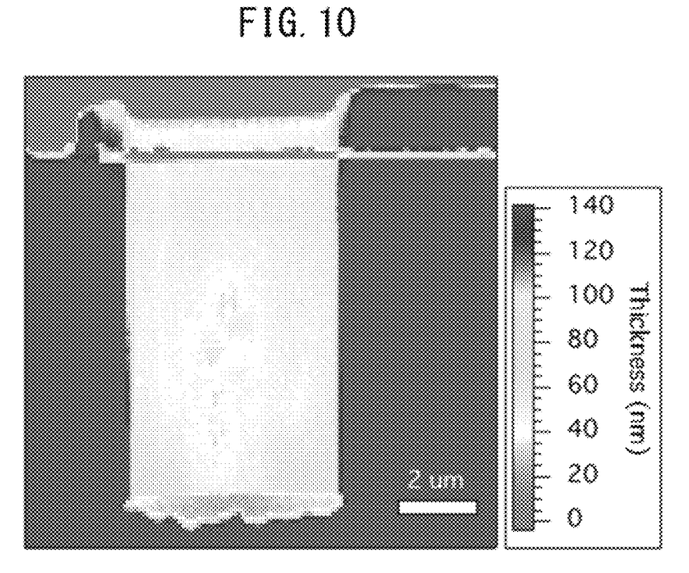
FIG. 10 shows thickness-distribution obtained from intensity of the transmission X-ray.

Next, the fabricated sample as shown in FIG. 9 is etched using focused ion beam. X-ray transmittance of the obtained sample is measured, followed by determining thickness distribution as shown in FIG. 10. The thickness of the sample can be determined from the following equation.

$$t=\lambda ln(I_0/I)$$

where, t is a sample thickness, $\lambda$ is substance-specific X-ray transmittance, $I_0$ is intensity of X-ray irradiation, I is intensity of transmission X-ray.

As shown in FIG. 10, the sample is found to be fabricated into 50 nm~1000 nm in thickness.

Figure 11:
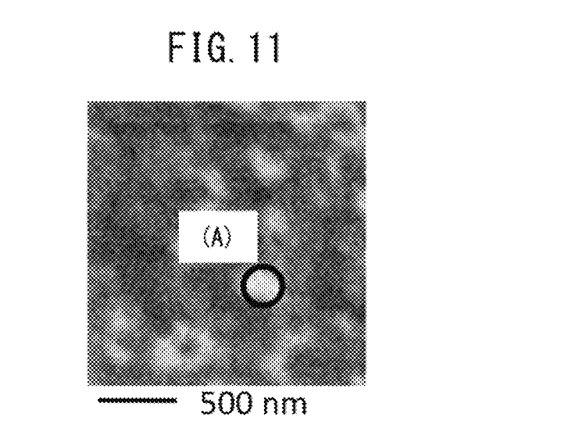
FIG. 11 shows an observed XMCD interval distribution.
Figure 12:
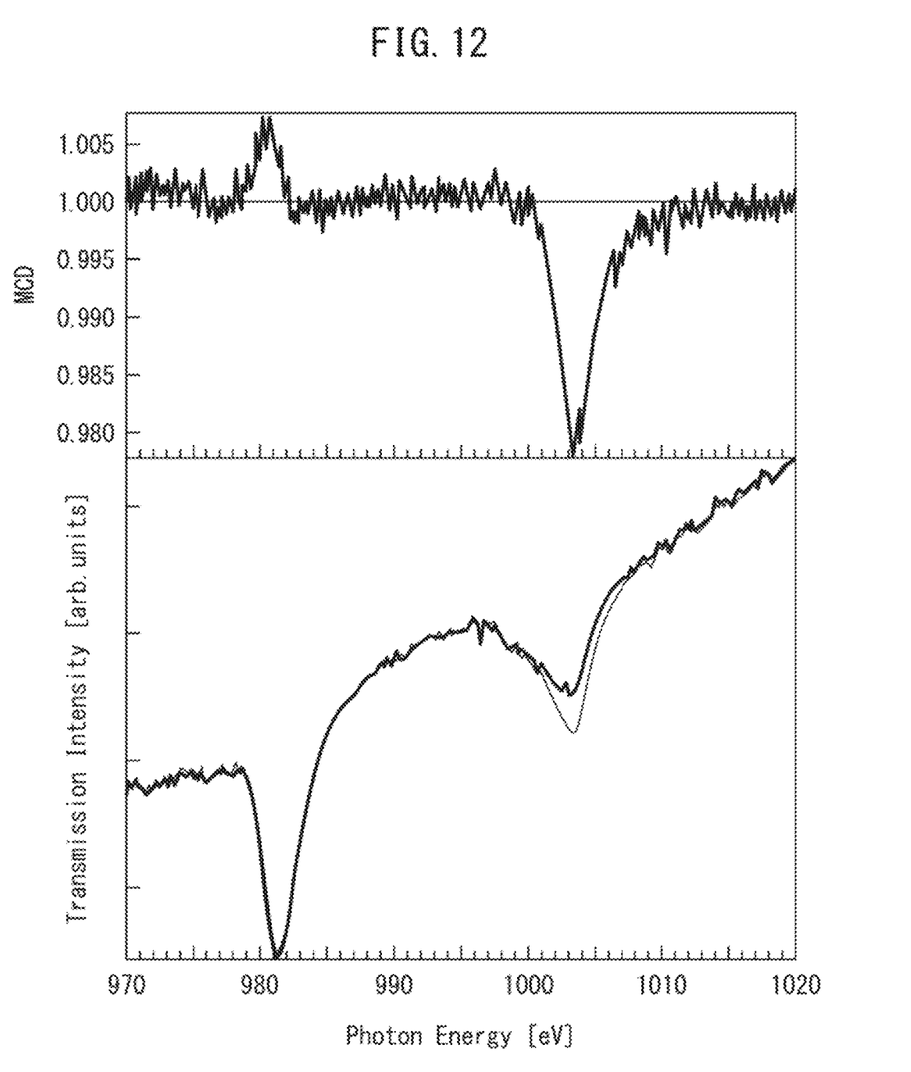
FIG. 12 shows a result of magnetic characteristic measurement.

Next, the fabricated sample is irradiated with circular polarization X-ray, followed by measuring magnetic characteristic. FIG. 11 shows a XMCD space distribution. In FIG. 11, the difference in contrasting density of white and black colors shows the difference for the direction of magnetic moment corresponding to the magnetic domain phase of magnetic body. The magnetic characteristic at the part (A) in FIG. 11 is found to have two peaks at 981 eV and 1003 eV, respectively, as shown in FIG. 12. From the spectrum analysis, it is found that the magnetism property such as spin magnetic momentum and orbital magnetic momentum can be measured for a single crystal particle.

EXPLANATION OF REFERENCE CHARACTERS 1 sample
2 focused ion beam
3 X-ray

The invention claimed is:

1. A magnetic measurement method comprising:
   measuring a magnetic characteristic of a single crystal particle of a magnetic sample of 50 nm~1000 nm in thickness by:
      irradiating the magnetic sample with X-ray that passes through at least one of a Fresnel zone plate (FZP) and an order-sorting aperture (OSA) that focuses X-ray flux passing through,
      detecting an intensity of transmissive X-ray passing through the single crystal particle, and
      determining, based on the detected intensity of transmissive X-ray passing through the single crystal particle, the magnetic characteristic of the single crystal particle.

2. The magnetic measurement method according to claim 1, wherein the X-ray is a circular polarization X-ray.

3. The magnetic measurement method according to claim 2, the method further comprising:
   alternately irradiating the single crystal particle with a right-circular polarization X-ray and a left-circular polarization X-ray,
   measuring X-ray absorption of each of the right-circular and left-circular polarization X-rays, respectively, and
   detecting X-ray magnetic circular dichroism (XMCD), which is a difference between two X-ray absorptions, of the single crystal particle based on the X-ray absorption measurement results.

4. The magnetic measurement method according to claim 2, further comprising:
   measuring X-ray absorption in the magnetic sample's magnetic field parallel to a direction of polarization light and X-ray absorption in the magnetic sample's magnetic field anti-parallel to the direction of polarization light, respectively, and
   detecting a difference between the two X-ray absorptions.

5. The magnetic measurement method according to claim 1, further comprising, prior to the measurement, fabricating the magnetic sample into a microtome section of 50 nm~1000 nm in thickness using focused ion beam etching.

6. The magnetic measurement method according to claim 1, wherein the measurement is carried out within an external magnetic field.

7. The magnetic measurement method according to claim 1, further comprising using an Avalanche photodiode (APD) to detect the intensity of transmission X-ray passing through the single crystal particle.

8. The magnetic measurement method according to claim 1, wherein the X-ray applied to the sample is circular polarization X-ray focused into 10 nm in beam size.

9. The magnetic measurement method according to claim 1, further comprising:
   generating right-circular polarization X-ray and left-circular polarization X-ray which enters a measurement place of the sample,
   successively detecting the transmission X-ray,
   alternately measuring the intensity of the transmission X-ray corresponding to right-circular polarization X-ray and the intensity of the transmission X-ray corresponding to left-circular polarization X-ray,
   detecting the difference between the two intensities, and
   determining the magnetization inside of the magnetic sample based on the detected difference between the two intensities.

10. A magnetic measurement system comprising:
    an X-ray source;
    a monochromator that converts right- and left-polarization X-ray of the X-ray source into right- and left-monochromatic X-ray;
    an aperture slit that allows the right- and left- monochromatic X-ray converted by the monochromator to pass through; and
    a processor configured to:
       measure a magnetic characteristic of a single crystal particle of a magetic sample of 50 nm~1000 nm in thickness by:
          causing the magnetic sample to he irradiated with X-ray that passes through at least one of a Fresnel zone plate (FZP) and an order-sorting aperture (OSA) that focuses X-ray flux passing through,
          detecting an intensity of transmission X-ray passing through the single crystal particle, and determining, based on the detected intensity of the transmissive X-ray passing through the single crystal particle, the magnetic characteristic of the single crystal particle.

11. The magnetic measurement system according to claim 10, further comprising: an analytical section having a combination of a Fresnel zone plate (FZP) that receives and focuses the right- and left-monochromatic X-ray on a single point wide of a magnetic sample, an order-sorting aperture (OSA) that allows the X-ray focused by the FZP to selectively pass through, and a sample-stage configured to set a comparatively thick magnetic sample that is more than 150 nm thick and less than or equal to 1000 nm thick to be irradiated with the X-ray.

12. A magnetic measurement apparatus comprising:
an analytical section having a combination of a Fresnel zone plate (FZP) that focuses X-ray received from a monochromator on a single point of a polycrystalline magnetic sample, and an order-sorting aperture (OSA) that allows the X-ray focused by the FZP to selectively pass through, a sample-stage that is configured to set the polycrystalline magnetic sample that is more than 150 nm thick and less than or equal to 1000 nm thick to be irradiated with the X-ray passing through the OSA; and
a processor configured to:
measure a magnetic characteristic of a single crystal particle of the magnetic sample of 50 nm~1000 nm in thickness by:
causing the magnetic sample to be irradiated with X-ray that passes through at least one of the FZP and the OSA,
detecting an intensity of transmission X-ray passing through the single crystal particle, and
determining, based on the detected intensity of the transmissive X-ray passing through the single crystal particle, the magnetic characteristic of the single crystal particle.

13. The magnetic measurement system according to claim 10, wherein the processor is configured to: generate two-dimensional X-ray magnetic circular dichroism (XMCD) data, based on the detected transmittance of the transmission X-ray, of each single crystalline-grain contained in the sample by directly measuring transmittance of transmission X-ray passing through the single crystalline-grains even within an external magnet field.

14. The magnetic measurement system according to claim 10, further comprising an Avalanche photodiode (APD) having dynamic ranges and optical fibers which are used within an external magnetic field, wherein the processor is configured to: use the APD to detect the intensity of transmission X-ray passing through the single crystal particle.

15. The magnetic measurement system according to claim 12, further comprising: piezoelectric devices that control X-, Y- and Z-stages, of the analytical section, which includes the sample-stage of the analytical section with accuracy in nanometers.

16. The magnetic measurement apparatus according to claim 12, further comprising: piezoelectric devices that control X-, Y- and Z-stages, of the analytical section, which includes the sample-stage of the analytical section with accuracy in nanometers.

17. The magnetic measurement apparatus according to claim 12, wherein the processor is configured to: generate two-dimensional X-ray magnetic circular dichroism (XMCD) data, based on the detected transmittance of the transmission X-ray, of each single crystalline-grain contained in the sample by directly measuring transmittance of transmission X-ray passing through the single crystalline-grains even within an external magnet field.

18. The magnetic measurement apparatus according to claim 12, further comprising an Avalanche photodiode (APD) having dynamic ranges and optical fibers which are used within an external magnetic field, wherein the processor is configured to: use the APD to detect the intensity of transmission X-ray passing through the single crystal particle.

19. The magnetic measurement apparatus according to claim 12, the X-ray applied to the sample is circular polarization X-ray focused into about 10 nm in beam size.

20. The magnetic measurement apparatus according to claim 12, wherein the processor is further configured to:
generate right-circular polarization X-ray and left-circular polarization X-ray to enter a measurement place of the sample,
successively detect the transmission X-ray,
alternately measure the intensity of the transmission X-ray corresponding to right-circular polarization X-ray and the intensity of the transmission X-ray corresponding to left-circular polarization X-ray,
detect the difference between the two intensities, and
determine the magnetization in the inside of the X-ray incident position based on the detected difference between the two intensities.

* * * * *